(12) United States Patent
Taylor et al.

(10) Patent No.: US 6,331,425 B1
(45) Date of Patent: Dec. 18, 2001

(54) RECOMBINANT PROTEIN HAVING BACTERIOPHAGE ENDOSIALIDASE ENZYMATIC ACTIVITY

(75) Inventors: Peter William Taylor, Billingshurst; John Paul Luzio, Little Eversden; Jonathan Mark Bryant, Exeter, all of (GB)

(73) Assignee: Endozyme Limited, West Sussex (GB)

( * ) Notice: Subject to any disclaimer, the term of this patent is extended or adjusted under 35 U.S.C. 154(b) by 0 days.

(21) Appl. No.: 08/983,275

(22) PCT Filed: Jul. 1, 1996

(86) PCT No.: PCT/GB96/01577

§ 371 Date: Apr. 2, 1998

§ 102(e) Date: Apr. 2, 1998

(87) PCT Pub. No.: WO97/02351

PCT Pub. Date: Jan. 23, 1997

(30) Foreign Application Priority Data

Jul. 5, 1995 (GB) .................................................. 9513683

(51) Int. Cl.[7] .............................. C12N 9/00; C12N 9/14; C12N 9/24; C12N 1/20
(52) U.S. Cl. ...................... 435/200; 435/69.1; 435/183; 435/195; 435/200; 435/252.3; 435/320.1; 435/252.33; 536/23.2; 424/96.1
(58) Field of Search ................................. 435/200, 195, 435/320.1, 252.3, 252.33; 536/23.2, 23.4; 424/94.6, 94.61

(56) References Cited

U.S. PATENT DOCUMENTS 4,695,541 9/1987 Taylor ..................................... 435/18
5,654,176 * 8/1997 Smith et al. ......................... 435/69.7

FOREIGN PATENT DOCUMENTS

| 0293249 A1 | 11/1988 | (EP) . |
| WO 93/06218 * | 4/1993 | (EP) . |
| 0587541 A1 | 3/1994 | (EP) . |
| 0 646 646 A3 | 6/1996 | (EP) . |
| WO 93/23544 | 11/1993 | (WO) . |

OTHER PUBLICATIONS

The Pharmacia Molecular and Cell Biology Catalog, 1993 Edition, pp. 69 and 80, 1993.*
R. Gerardy–Schahn et al., Molecular cloning and functional expression of bacteriophage PK1E–encoded endonceraminidase Endo NE, Molecular Microbiology, 16: (3), 441–450 (1995).
Tomlinson et al., Neuraminidase Associated with Coliphage E That Specifically Depolymerizes the *Escherichia coli* K1 Capsular Polysaccharide, Journal of Virology, 55, No. 2, 374–378 (1985).
J.G.Petter and E.R. Vimr, Complete Nucleotide Sequence of the Bacteriophage K1F Tail Gene Encoding Endo–N–Acylneuraminidase (Endo–N) and Comparison to an Endo–N Homolog in Bacteriophage PK1E, Journal of Bacteriology, 175: No. 14, 4354–4363 (1993).

* cited by examiner

*Primary Examiner*—Rebecca Prouty
*Assistant Examiner*—Manjunath N. Rao
(74) *Attorney, Agent, or Firm*—Heslin Rothenberg Farley & Miesit P.C.

(57) ABSTRACT

A recombinant protein having bacteriophage endosialidase enzymatic activity obtainable by expression from a recombinant vector comprising a DNA sequence encoding a bacteriophage endosialidase linked to a DNA sequence of an expression vector which express a polypeptide which adds to the N-terminus of the endosialidase, or an analogue of said protein, which is a mutant, functional fragment or derivative of said protein having endosialidase enzymatic activity.

18 Claims, No Drawings

RECOMBINANT PROTEIN HAVING BACTERIOPHAGE ENDOSIALIDASE ENZYMATIC ACTIVITY

PRIOR FOREIGN APPLICATIONS

This application is a 35 USC §371 filing of PCT/GB96/01577, filed Jul. 1, 1996 and claims priority from GB Patent Application Number 9513683.4, filed July 5, 1995.

This invention relates to a recombinant protein having bacteriophage endosialidase activity, to a process for the production thereof and to recombinant expression systems for use in the production thereof.

Bacteriophage E is a member of the PK1A–PK1E family of phages; these phages were isolated originally from European sewage to aid in the clinical identification of *Escherichia coli* K1 infections, which can result in high mortality rates in cases of neonatal meningitis. Bacteriophage E endosialidase (K I E endosialidase) is thought to be the enzyme responsible for initial binding to host bacteria by specifically recognising and hydrolysing the α-2,8-linked poly-N-acetylneuraminic acid (polysialic acid/PSA) carbohydrate polymers of the K1 glycocalyx. α-2,8-linked PSA is also expressed on the cell surface of several other pathogenic bacteria, and various tumour cells and cell lines. It has been proposed in U.S. Pat. No. 4,695,541 that K1E endosialidase could be used in the diagnosis and therapy of K1 meningitis, septicaemia or bacteraemia due to the enzyme's high specificity for hydrolysing α-2,8-sialosyl linkages. PSA has been suggested as an oncodevelopmental marker in human tumours of the kidney and neuroendocrine tissues and also may contribute to the invasive and metastatic potential of some tumours.

In J. Bacteriol., 1993, 175, 4354–4363, there are described attempts to obtain enzymatically active protein by expression from a DNA construct derived from the related KIF phage; these attempts were unsuccessful.

It has now been found that protein having bacteriophage endosialidase enzymatic activity, i.e. a protein which specifically binds to or cleaves α-2,8-polysialic acid, can be obtained by expression from a DNA construct which is derivable from the KIE endosialidase gene and is cloned into an expression vector which expresses a polypeptide which adds to the N-terminus of the endosialidase sequence.

Accordingly, the present invention provides, in one aspect, a recombinant protein having bacteriophage endosialidase enzymatic activity obtainable by expression from a recombinant vector comprising a DNA sequence encoding a bacteriophage endosialidase linked to a DNA sequence of an expression vector which expresses a polypeptide which adds to the N-terminus of the endosialidase, or an analogue of said protein which is a mutant, functional fragment or derivative of said protein having endosialidase enzymatic activity.

The mutant may be, for example, a protein having an amino acid substituted or deleted at one or more positions- The functional fragment may be C- or N-terminal shortened fragment or a fragment from within the polypeptide chain which has endosialidase enzymatic activity. The derivative may be, for example, a pharmaceutically acceptable salt with an acid such as hydrochloric acid, sulphuric acid, phosphoric acid, pyrophosphoric acid, benzenesulphonic acid, p-toluenesulphonic acid, methanesulphonic acid, lactic acid, palmic acid, tartaric acid, ascorbic acid, or citric acid; with a base, usually a nitrogen containing base such as sodium, potassium, magnesium or ammonium nitrogen-containing base; or an internal salt.

In another aspect, the present invention provides a recombinant vector comprising a DNA sequence encoding a bacteriophage endosialidase linked to a DNA sequence of an expression vector which expresses a polypeptide which adds to the N-terminus of the endosialidase, said recombinant vector being capable of directing expression of said protein in a compatible host cell.

In a further aspect the present invention provides a process for the production of a protein having bacteriophage E endosialidase enzymatic activity which comprises culturing a host cell transformed with a recombinant vector as hereinbefore defined under conditions allowing expression of said protein and isolating the protein thereby produced. In a yet further aspect, the present invention provides a host cell transformed with a recombinant vector as hereinbefore defined.

Preferred protein according to the invention is a protein obtainable by expression from a recombinant vector as hereinbefore defined in which the DNA sequence encoding the endosialidase is derived from a DNA construct encoding amino acid residues encoded by nucleotides 172 to 1744 of the bacteriophage E endosialidase gene, i.e. nucleotides 172 to 1744 of SEQ ID No. 1 as hereinafter defined, or a mutant, functional fragment or derivative of said protein which has endosialidase enzymatic activity. An especially preferred protein according to the invention is a protein obtainable by expression from a recombinant vector as hereinbefore defined in which the DNA sequence encoding the endosialidase is derived from a DNA construct encoding amino acid residues encoded by nucleotides 1 to 2436 of the bacteriophage E endosialidase gene, i.e. nucleotides 1 to 2436 of SEQ. ID NO. 1 as hereinafter defined, or a mutant, functional fragment or derivative of said protein having endosialidase enzymatic activity The protein of the invention is generally expressed in the form of a fusion protein comprising the endosialidase linked, directly or through a spacer, to a polypeptide derived from the expression vector, i.e. the vector used for expression of the protein in a suitable host cell, a preferred such polypeptide being glutathione S-transferase. Where it is desired that the polypeptide components of the fusion protein should be separable, if the fusion protein does not naturally contain a region which can be specifically cleaved chemically or enzymatically, such a region can be inserted using conventional procedures. Examples of selective cleaving reagents or cleaving enzymes for fusion proteins are V8 protease, trypsin, thrombin, factor X, CNBr, peptidase yscα and yscF.

In a particularly preferred embodiment of the invention, the protein of the invention is in the form of a fusion protein comprising bacteriophage E endosialidase linked to glutathione S-transferase, the fusion protein preferably having a molecular weight of about 100 kDa.

A DNA construct, i.e. recombinant DNA molecule, suitable for the expression of a protein according to the invention may be an isolated DNA fragment encoding a bacteriophage endosialidase, for example consisting only of the coding region or prolonged by homologous or heterologous DNA sequences. The construct may be a DNA fragment encoding the endosialidase cloned into a suitable cloning vector, preferably a bacterial vector such as pBR317, pBR322, pUC18, pSF2124 or, especially, Bluescript SK+. Where such a clone lacks convenient restriction sites with which to isolate solely the endosialidase open reading frame, it may be amplified by a polymerase chain reaction (PCR) using primers incorporating the restriction sites required.

The DNA fragment encoding the bacteriophage endosialidase may be obtained from genomic bacteriophage E DNA or a synthetic DNA that is substantially homologous thereto, i.e. is 80–100% homologous thereto. Bacteriophage E can be purified and total genomic DNA can be extracted using conventional procedures. The extracted DNA can then be digested with an appropriate restriction enzyme such as Bgl II, Eco RI, Hinc II, Hind III, Bam HI or Pst I. The digestion product can be subjected to preparative electrophoresis with low-melting point agarose gel to enrich DNA fractions of a certain length in order to enrich DNA fragments encoding the protein of the invention.

When a nucleotide sequence encoding the bacteriophage endosialidase, or an amino acid sequence thereof, is known, DNA encoding the endosialidase can also be prepared by methods leading directly to the desired DNA such as conventional PCR procedures or in vitro chemical synthesis.

For expression of a protein of the invention, the DNA construct is cloned into an expression vector which expresses a polypeptide which adds to the N-terminus of the endosialidase to give a recombinant vector according to the invention. The expression vector is, of course, chosen according to the nature of the host cell chosen for expression of the protein. Suitable such expression vectors are available commercially. Expression is preferably carried out in a prokaryotic host, more preferably a microbial host, especially $E.$ $coli$, when a suitable expression vector is a prokaryotic expression vector such as a phage $\lambda$ or a bacterial plasmid. Examples of particular prokaryotic expression vectors are pGEX vectors, e.g. pGEX-2T (Pharmacia Biotech), which result in the expression of an endosialidase—glutathione S-transferase (GST) fusion protein, pMAL (New England Biolabs) which results in expression of an endosialidase—maltose binding protein fusion protein, the 'pinpoint' system from Promega which biotinylates expressed protein, the 'strep-tag' system from Biometra which places a streptavidin binding peptide on expressed protein, the Ni-NTA system from Qiagen which adds 6 histidines to expressed protein to bind nickel, and the Xpress system from Invitrogen working on a similar principle to the Ni-NTA system.

Preferred expression vectors are pGEX vectors, which have a tac promoter, an internal lac $I^q$ gene and a thrombin or factor $X_a$ protease recognition site, especially pGEX-2T which has the sequence:
Leu Val Pro Arg Gly Ser Pro Gly Ile His Arg Asp
CTG GTT CCG CGT GGA TCC CCG GGA ATT CAT CGT
GAC TGA CTG ACG Cloning of the DNA construct into the expression vector to give the recombinant vector of the invention may be carried out using conventional restriction and ligation techniques. Thus, where the DNA construct contains Bam HI and EcoRI restriction sites, which may have been incorporated by PCR amplification, the DNA construct and the expression vector may be digested simultaneously with Bam HI and EcoRI and ligation effected using a DNA ligase in accordance with the manufacturer's instructions.

As mentioned hereinbefore, the host cells used for expression of a protein of the invention are preferably prokaryotic, more preferably microbial cells, including cells of bacteria such as *Bacillus subtilis, Pseudomonas, Streptococcus* or, especially, *E. coli*.

Transformation of the host cells may be carried out using conventional techniques appropriate for those cells. Accordingly, the transformation procedure for *E. coli* cells includes, for example, $Ca^{2+}$ pretreatment of the cells so as to allow DNA uptake, and incubation with the recombinant vector. The subsequent selection of the transformed cells can be achieved, for example, by transferring the cells to a selective growth medium which allows separation of the transformed cells from the parent cells, or by restriction analysis of a miniprep DNA sample obtained from the incubated cells.

The transformed host cells may be cultured by methods known in the art in a liquid medium containing an assimilable source of carbon, e.g. a carbohydrate such as glucose or lactose, nitrogen, e.g. an amino acid, peptide, protein or degradation product thereof such as a peptone, ammonium salt or the like, and an inorganic salt, e.g. a sulfate, phosphate and/or carbonate of sodium, potassium, magnesium or calcium. The medium may also contain, for example, a growth-promoting substance, such as a trace element, for example iron, zinc, manganese and the like.

Culturing may be effected by processes which are known in the art. The culture conditions, such as temperature, pH value of the medium and fermentation time, are chosen so that a maximum expression level of the protein of the invention is obtained. Thus, an *E. coli* strain is preferably cultured under aerobic conditions by submerged culture with shaking or stirring at a temperature of about 20° C. to 40° C., preferably at about 37° C., and a pH value of 4 to 8, preferably of about 7, for about 4 to 30 hours, preferably until maximum yields of the protein of the invention are reached.

The expressed protein can be extracted from microbial cells such as *E. coli* cells or a supernatant of a cell culture by conventional methods, e.g. comprising lysis of the cells, chromatography such as ion-exchange, hydrophobic or size-exclusion chromatography, precipitation, e.g. with ammonium sulfate or acid, preparative electrophoresis such as sodium dodecyl sulphate—polyacrylamide gel electrophoresis (SDS-PAGE) or isoelectric focussing, and the like. When, as in especially preferred embodiments of the invention, the expressed protein is an endosialidase-glutathione S-transferase fusion protein, this may be purified by binding to glutathione beads as described by Smith and Johnson (1988) Gene 67, 31–40. Cleavage of the purified fusion protein can be effected with thrombin, for example following the instructions of Pharmacia Biotech, manufacturers of the pGEX-2T expression vector.

The present invention also provides a pharmaceutical composition comprising as active ingredient a protein of the invention or a pharmaceutically acceptable salt thereof, optionally together with a physiologically acceptable carrier, which may be, for example, an excipient, diluent or other conventional auxilliary in pharmaceutical compositions.

Proteins of the invention may be used in the diagnosis or treatment of medical conditions, especially of the human body, including various diseases, particularly meningitis and cancers characterised by expression of polysialic acid on the surface of the tumour cell, such as Wilm's Kidney Tumour, small cell lung carcinoma, neuroblastoma, medullary thyroid carcinoma, urinary tract tumour, neuroectodermal tumour, teratoma, rhabdomyosarcoma, pheochromocytoma, Ewing's sarcoma, insulinoma, breast cancer and pituitary tumour. The proteins may be used to inhibit tumour metastasis, for example post-surgical metastasis. The proteins may also be used in the diagnosis or treatment of other conditions caused by *E. coli* KI, such as sepsis and urinary tract infections, or by other bacteria expressing polysialic acid on the cell surface thereof.

Thus the present invention also provides a method of treating a condition caused by a bacterium expressing polysialic acid on a cell surface thereof, cancer characterised by expression of polysialic acid on a tumour cell surface, or tumour metastasis, which comprises administering a protein or analogue of the invention as hereinbefore defined to a warm-blooded mammal in need of such treatment.

A pharmaceutical composition of the invention, particularly for the above indications, may be administered parenterally, for example intravenously, intracutaneously, subcutaneously or intramuscularly. The dosage depends principally on the method of administration and on the purpose of the treatment. Individual doses and the administration regime can best be determined by individual judgement of a particular case of illness. Usually, a therapeutically effective amount of a protein of the invention, when administered by injection, is from about 0.005 to about 0.1 mg/kg body weight.

In addition to the active ingredient, an injectable pharmaceutical composition of the invention may contain a buffer, for example a phosphate buffer, sodium chloride, mannitol or sorbitol to adjust the isotonicity, and an antibacterially active preservative such as the methyl or ethyl ester of p-hydroxybenzoic acid.

The proteins of the invention, in view of their enzymatic activity, may also be used in the analysis of glycoproteins, for example detection and sequencing of oligosaccharide moieties decorating glycoproteins, since they can selectively remove particular sugar residues from the glycoproteins.

The invention is illustrated by the following Examples, which relate to especially preferred embodiments.

EXAMPLE 1

Preparation of DNA Construct Containing Bacteriophage E Endosialidase Open Reading Frame Unless otherwise stated, all procedures used are as described by Sambrook et al, Molecular Cloning: a Laboratory Mannual, 2nd Edition, Cold Spring Harbor Laboratory Press, N.Y. (1989).

Degenerate oligonucleotide probes are designed with reference to *E. coli* codon usage tables (Holm (1986) Nuc. Acids Res. 14, 3075–3087), prepared using an automated Applied Biosystems PCR—MATE model 391 DNA synthesiser and 5' end-labelled with [Y-$^{32}$P]ATP (Amersham International Plc., Amersham, Bucks, U.K.) using T4 polynucleotide kinase. The radiolabelled oligonucleotide probes are hybridised to restriction enzyme digests of bacteriophage E DNA, electrophoresed in agarose gels and transferred to Hybond-N nylon membrane (Amersham International Plc.). Bacteriophage E DNA fragments reacting with the probes are identified by autoradiography, purified from NA grade agarose gels (Pharmacia Biosystems Ltd, Milton Keynes, Bucks, U.K.) and ligated into Bluescript SK+ (Strategene Inc., La Jolla, Calif., USA) using T4 DNA ligase (NEB Inc.). Transformations of *E. coli* Epicurian SURE cells (Strategene Inc.) with Bluescript SK+ are conducted according to an electroporation method (Dower et al (1988) Nucleic Acids Res. 16, 6127–6145) using a Bio-Rad Gene Pulser and Pulse Controller, or alternatively high efficiency *E. coli* JM109 competent cells (Promega Inc. Madison, Wis., USA) are transformed by heat shock at 42° C. for 60 sec. Clones transformed with recombinant plasmid are identified by growing on 2TY/ampicillin agar plates and using a mixture of 50 mg/ml 5-bromo-4-chloro-3-indoyl-β-D-galactopyranoside (X-Gal) and 0.1M isopropyl β-D-thiogalactopyranoside (IPTG) to allow blue-white colour selection of colonies. Double stranded DNA sequencing is conducted using the Sequenase Version 2.0 sequencing kit from United States Biochemical Corporation, Cleveland, Ohio, USA and a model SA sequencing apparatus from BRL Life Technologies Inc., Gaithersburg, Md., U.S.A. Sequencing is facilitated by the technique of nested deletions or by using synthetic oligonucleotide primers prepared by British Bio-technology Products Ltd, Abingdon, Oxon, U.K. or as above.

A degenerate oligonucleotide probe, Probe 1 [5'-TAC(T)CAC(T)CAGGGT(G)GAC (T)GTG(T)GCG(C)CC-3'], is derived from the cyanogen bromide fragment of KIE endosialidase with the longest unambiguous amino acid sequence, and is the least degenerate of five probes designed using the partial amino acid sequences obtained from the cyanogen bromide fragments. A 1.9 kb BglII restriction digest fragment of genomic bacteriophage E DNA is identified as potentially encoding endosialidase sequence by Southern blot analysis using $^{32}$P-radiolabelled probe 1. BglII and BamHI restriction endonucleases generate cohesive protruding ends with the same sequence and this enables the ligation of the 1.9 kb BglII fragment into the BamHI site of Bluescript SK$_+$ cloning vector (Promega Inc). Plasmid miniprep DNA from a clone transformed with the resultant recombinant vector (Clone 1) yields DNA sequence which encodes a deduced protein sequence containing a stretch of sequence identical to that of the CNBr fragment used to design Probe 1.

Probe 2 [5'-GATCTTGGTCTAATCCCT-3'], a non-degenerate oligonucleotide 18-mer, is synthesised using the sequence at the 5' end of Clone 1. This probe identifies one of two Sin1 digest fragments of genomic bacteriophage E DNA which runs as a singlet equivalent to about 3.3 kb. It is verified that this fragment codes for DNA sequence upstream of the 5' end of Clone 1 by digesting the Clone 1 insert DNA with Sin1. The result of this digest shows there are at least 3 Sin1 sites in the Clone 1 insert DNA, the largest fragment being 1.1 kb. Since restriction analysis of bacteriophage E DNA shows that there are only two BglII sites in the whole genome, the gel purified Sin1 fragments are digested with BglII and the fragment containing the probe 2 recognition sequence and the BglII site yields two fragments of 2.1 kb and 1.1 kb. The 2.1 kb Sin1×BglII digest fragment is cloned into Bluescript SK+ by ligation of the BglII end to a BamHI end, followed by end-filling using the Klenow fragment of T4 DNA polymerase and ligating the resultant blunt ends together to circularise the plasmid. The resultant clone (Clone 2) is found to contain an open reading frame encoding the N-terminus of KIE endosialidase by comparison with the N-terminal amino acid sequence of the ~76 kDa enzyme subunit. Overlapping sequence is obtained for clones 1 and 2 in both 5' and 3' directions, and the positions of open reading frames are determined by codon preference and positional base preferences analysis (Staden et al, (1982) Nuc. Acids Res. 10, 141–156 and Staden (1990) Meth. Enzymol. 183, 163–180).

Recombinant plasmid DNA is purified from Clone 2, linearised by cleavage of the unique EcoRI site and 5' capped RNA is transcribed using SP6 RNA polymerase and mCAP mRNA capping kit (Stratagene Inc.). In vitro translation reactions (25 μl) using 0.1 μg RNA transcript, 20 μCi [$^{35}$S] methionine and a rabbit reticulocyte lysate system are carried out according to manufacturer's instructions (Promega Inc.). Confirmation that the SP6 RNA polymerase and the in vitro translation system are functional is obtained by running a positive control alongside. The control plasmid is a linearised SV64-carboxypeptidase E construct with an upstream SP6 promoter region (Fricker et al, (1989) Mol. Endocrinol. 3, 666–673).

A fragment of bacteriophage E DNA of 1892 bp containing the complete Clone 1 insert is excised from Clone 1 using EcoRI and XbaI. This is directionally cloned into the vector pGEM-IIz (Promega Inc.) cut with the same restriction enzymes thus placing a SacI site 3' of the Clone 1 insert. A 707 bp SacI/AvrII fragment is excised from this new construct. This 707 bp fragment encodes the predicted C-terminal 114 amino acids of the endosialidase and the 3' untranslated region of KIE DNA. It is ligated into the 3253 bp product of a SacI/AvrII digest of Clone 2. The resulting plasmid (Clone 3) contains only the extreme 5' and 3' regions of the originally cloned KIE DNA in a Bluescript SK+ vector effectively lacking the central 2975 bp of the DNA sequence which includes the sequence encoding the predicted endosialidase open reading frame. A 2975 bp fragment derived from an AvrII digest of total KIE DNA is ligated into Clone 3 digested with AvrII. The resulting construct in Bluescript SK+ (Clone 4) contains the full length endosialidase gene previously encoded in Clones 1 and 2, and the gene is sequenced using the Sequenase 2.0 sequencing kit (USB Corp). It has the sequence shown in SEQ. ID. No: 1.

EXAMPLE 2

Preparation of Recombinant Plasmid for Expression of Bacteriophage E Endosialidase Clone 4, the DNA construct containing the complete endosialidase open reading frame prepared as described in Example 1, is subjected to PCR using primers
5'-CCGGGGATCCATGATTCAAAGACTAGGTTCTTC ATTA-3' and
3'-CGTTAGACGACGTGCGGTCTTGTGTATCTTMA GACAC-5' to facilitate amplification of the endosialidase open reading frame with incorporation of a BamHI restriction site and an EcoRI restriction site at the 5' and 3' termini of the open reading frame respectively.

The 2483 bp PCR product is cleaned by extraction first with a mixture of equal volumes of phenol (equilibrated to pH 8.0 with 2-amino-2-hydroxymethylpropane-1,3-diol) and a 24:1 mixture of chloroform and isoamyl alcohol, then with the chloroform: isoamyl alcohol mixture alone, followed by precipitation in ethanol and resuspension in TE buffer (10 mM 2-amino-2-hydroxymethylpropane-1,3-diol hydrochloride, 1 mM EDTA, pH8.0). The cleaned PCR product and pGEX-2T expression vector (Pharmacia Biotech) are digested simultaneously with BamHI and EcoRI and purified by agarose gel electrophoresis and Qiaex extraction (Quiagen Corp). The cut PCR product and expression vector are ligated using T4 DNA ligase (New England Biolabs) according to the manufacturer's instructions, to form a recombinant vector, which is sequenced, using USB Sequenase 2.0, across the two cloning sites to verify that the correct reading frame has been maintained.

Example 3

Transformation and Expression

The ligation product of Example 2 is used to transform electrocompetent E. coli MC 1061 cells using a Bio Rad electroporation apparatus and the transformed cells are selected by restriction analysis of a miniprep DNA sample obtained from the cells.

The transformed cells are cultured to express a fusion protein by the addition of IPTG to a final concentration of 0.5 mM, when the $OD_{600}$ has reached 0.3, and are then allowed to grow for a further 4 hours at 37° C. with shaking at 250 rpm. The expressed fusion protein is purified from the culture medium by binding to glutathione beads as described by Smith and Johnson (1988) Gene 67, 31–40.

Samples of the bacterial culture and of purified fusion protein fractions are subjected to SDS-PAGE, electrophoretically transferred to a nitrocellulose membrane, washed and hybridised to antiendosialidase polyclonal antiserum by the method of Sambrook et al, (1989), op. cit. Immunoreactive bands are detected by binding a second antibody conjugated to alkaline phosphatase and reaction with (a) a 50 mg/ml solution of nitroblue tetrazolium chloride in a 70:30 mixture of dimethylformamide and water and (b) a 50 mg/ml solution of 5-bromo-4-chloro-3-indolyl phosphate disodium salt in water.

The release of N-acetylneuraminic acid (NANA) from polysialic acid by purified fractions of the fusion protein is measured using the TBA assay of Horgan (1981) Clin. Chim. Acta 116, 409–415. The measurements show that rate of release of NANA is directly proportional to fusion protein concentration. No release of NANA is observed when the fusion protein is replaced by glutathione S-transferase protein alone.

What is claimed is:

1. An isolated and purified polynucleotide consisting of nucleotides 172 to 1744 of SEQ ID NO:1.

2. A recombinant fusion protein obtained by expression of a recombinant expression vector comprising nucleotides 172 to 1744 of SEQ ID No:1, encoding a bacteriophage endosialidase and linked to a polynucleotide sequence that can express, a polypeptide such that said polypeptide is added to the N-terminus of said bacteriophage endosialidase either directly or through a spacer sequence.

3. A recombinant fusion protein, according to claim 2, wherein said polypeptide is glutathione S-transferase.

4. A recombinant fusion protein according to claim 3, comprising bacteriophage E endosialidase linked to glutathione S-transferase.

5. A recombinant fusion protein obtained by expression of a recombinant expression vector comprising nucleotides 1–2436 of SEQ ID NO:1, encoding it bacteriophage endosialidase and linked to a polynucleotide sequence that can express a polypeptide such that said polypeptide is added to the N-terminus of said bacteriophage endosialidase either directly or through a spacer sequence.

6. A recombinant fusion protein, according to claim 5, wherein said polypeptide is glutathione S-transferase.

7. A recombinant fusion protein according to claim 6, comprising bacteriophage E endosialidase linked to glutathione S-transferase.

8. A recombinant expression vector comprising nucleotides 172 to 1744 of SEQ ID NO:1, encoding a bacteriophage endosialidase and linked to a polynucleotide sequence that can express a polypeptide such that said polypeptide is added to the N-terminus of said bacteriophage endosialidase wherein said recombinant expression vector is capable of directing expression of a recombinant fusion protein having bacteriophage endosialidase enzyme activity in a compatible host cell.

9. A host cell transformed with a recombinant vector according to claim 8.

10. A host cell according to claim 9 which is a transformed microbial cell.

11. A host cell according to claim 10 which is a transformed E. Coli cell.

12. A recombinant vector according to claim 8 wherein the expression vector is a prokaryotic expression vector.

13. A recombinant vector according to claim 12 wherein the expression vector is a pGEX vector.

14. A recombinant vector according to claim 13 wherein the expression vector is pGEX-2T.

15. A process for the production of a recombinant fusion protein having bacteriophage endosialidase enzyme activity, said process comprising:

culturing a host cell transformed with a recombinant expression vector comprising nucleotides 172 to 1744 of SEQ ID NO:1, encoding a bacteriophage endosialidase and linked to a polynucleotide sequence that can express a polypeptide such that said polypeptide is added to the N-terminus of said bacteriophage endosialidase wherein said recombinant expression vector is capable of directing expression of a recombinant fusion protein having bacteriophage endosialidase enzyme activity in a compatible host cell, under conditions allowing expression of said recombinant fusion protein; and isolating the recombinant fusion protein thereby produced.

16. A process according to claim 15 wherein the host cell is a microbial cell.

17. A process according to claim 16 wherein the host cell is an *E. coli* cell.

18. A pharmaceutical composition comprising a recombinant fusion protein, according to claim 2, or a pharmaceutically acceptable salt thereof, and a physiologically acceptable carrier.

* * * * *

UNITED STATES PATENT AND TRADEMARK OFFICE
CERTIFICATE OF CORRECTION

PATENT NO.    : 6,331,425 B1
DATED         : December 18, 2001
INVENTOR(S)   : Taylor et al.

It is certified that error appears in the above-identified patent and that said Letters Patent is hereby corrected as shown below:

Title page,
ABSTRACT, line 5, delete "express" and insert -- expresses --

Column 19, claim 5,
Line 57, delete "it" and insert -- a --

Signed and Sealed this

Sixteenth Day of April, 2002

Attest:

JAMES E. ROGAN
*Attesting Officer*  *Director of the United States Patent and Trademark Office*

SEQUENCE LISTING

```
<160> NUMBER OF SEQ ID NOS: 8

<210> SEQ ID NO 1
<211> LENGTH: 2436
<212> TYPE: DNA
<213> ORGANISM: Bacteriophage E
<220> FEATURE:
<221> NAME/KEY: CDS
<222> LOCATION: (1)..(2436)
<223> OTHER INFORMATION: coding region for bacteriophage E endosialidase

<400> SEQUENCE: 1 atg att caa aga cta ggt tct tca tta gtt aaa ttc aag agt aaa ata      48
Met Ile Gln Arg Leu Gly Ser Ser Leu Val Lys Phe Lys Ser Lys Ile
  1               5                  10                  15 gca ggt gca atc tgg cgt aac ttg gat gac aag ctc acc gag gtt gta      96
```

-continued

| | |
|---|---|
| Ala Gly Ala Ile Trp Arg Asn Leu Asp Asp Lys Leu Thr Glu Val Val<br>20                             25                        30 | |
| tcg ctt aaa gat ttt gga gcc aaa ggt gat ggt aag aca aac gac caa<br>Ser Leu Lys Asp Phe Gly Ala Lys Gly Asp Gly Lys Thr Asn Asp Gln<br>        35                        40                        45 | 144 |
| gat gca gta aat gca gcg atg gct tca ggt aag aga att gac ggt gct<br>Asp Ala Val Asn Ala Ala Met Ala Ser Gly Lys Arg Ile Asp Gly Ala<br>50                        55                       60 | 192 |
| ggt gct act tac aaa gta tca tct tta cct gat atg gag cga ttc tat<br>Gly Ala Thr Tyr Lys Val Ser Ser Leu Pro Asp Met Glu Arg Phe Tyr<br>65                       70                     75                    80 | 240 |
| aac acc cgc ttc gta tgg gaa cgt tta gca ggt caa cct ctt tac tat<br>Asn Thr Arg Phe Val Trp Glu Arg Leu Ala Gly Gln Pro Leu Tyr Tyr<br>                 85                        90                    95 | 288 |
| gtg agt aaa ggt ttt atc aat ggt gaa ctc tat aaa atc acg gat aac<br>Val Ser Lys Gly Phe Ile Asn Gly Glu Leu Tyr Lys Ile Thr Asp Asn<br>        100                      105                     110 | 336 |
| cct tat tac aat gct tgg cct caa gac aaa gcg ttt gta tat gag aac<br>Pro Tyr Tyr Asn Ala Trp Pro Gln Asp Lys Ala Phe Val Tyr Glu Asn<br>             115                     120                     125 | 384 |
| gtg ata tat gca cct tac atg ggt agc gac cgt cat ggt gtt agt cgt<br>Val Ile Tyr Ala Pro Tyr Met Gly Ser Asp Arg His Gly Val Ser Arg<br>130                        135                     140 | 432 |
| ctg cat gta tca tgg gtt aag tct ggt gac gat ggt caa aca tgg tct<br>Leu His Val Ser Trp Val Lys Ser Gly Asp Asp Gly Gln Thr Trp Ser<br>145                        150                     155                    160 | 480 |
| act cca gag tgg tta act gat atg cat cca gat tac cct aca gtg aac<br>Thr Pro Glu Trp Leu Thr Asp Met His Pro Asp Tyr Pro Thr Val Asn<br>             165                     170                     175 | 528 |
| tat cat tgt atg agt atg ggt gta tgt cgc aac cgt ctg ttt gcc atg<br>Tyr His Cys Met Ser Met Gly Val Cys Arg Asn Arg Leu Phe Ala Met<br>                 180                     185                     190 | 576 |
| att gaa aca cgt act tta gcc aag aac gaa cta acc aat tgt gca ttg<br>Ile Glu Thr Arg Thr Leu Ala Lys Asn Glu Leu Thr Asn Cys Ala Leu<br>             195                     200                     205 | 624 |
| tgg gat cgc cct atg tct cgt agt ctg cat ctt act ggt ggt atc act<br>Trp Asp Arg Pro Met Ser Arg Ser Leu His Leu Thr Gly Gly Ile Thr<br>210                        215                     220 | 672 |
| aag gct gca aat cag aga tat gca aca atc cat gta cct gat cac gga<br>Lys Ala Ala Asn Gln Arg Tyr Ala Thr Ile His Val Pro Asp His Gly<br>225                        230                     235                    240 | 720 |
| ctc ttc gtt ggt gat ttt gtt aac ttc tct aac tct gcg gta aca ggt<br>Leu Phe Val Gly Asp Phe Val Asn Phe Ser Asn Ser Ala Val Thr Gly<br>                 245                     250                     255 | 768 |
| gta tct ggt gat atg aag gtt gca aca gta ata gat aag gac aac ttc<br>Val Ser Gly Asp Met Lys Val Ala Thr Val Ile Asp Lys Asp Asn Phe<br>        260                      265                     270 | 816 |
| acg gtt ctt aca cct aac cag cag act tca gat ttg aat aac gct gga<br>Thr Val Leu Thr Pro Asn Gln Gln Thr Ser Asp Leu Asn Asn Ala Gly<br>             275                     280                     285 | 864 |
| aag aat tgg cac atg ggt act tct ttc cat aag tct ccg tgg cgt aag<br>Lys Asn Trp His Met Gly Thr Ser Phe His Lys Ser Pro Trp Arg Lys<br>        290                      295                     300 | 912 |
| aca gat ctt ggt cta atc cct cgt gtc aca gag gtg cat agc ttt gct<br>Thr Asp Leu Gly Leu Ile Pro Arg Val Thr Glu Val His Ser Phe Ala<br>305                        310                     315                    320 | 960 |
| act att gat aac aat ggc ttt gtt atg ggc tat cat caa ggt gat gta<br>Thr Ile Asp Asn Asn Gly Phe Val Met Gly Tyr His Gln Gly Asp Val<br>             325                     330                     335 | 1008 |

-continued

| | | |
|---|---|---|
| gct cca cga gaa gtt ggg ctt ttc tac ttc cct gat gct ttc aat agc<br>Ala Pro Arg Glu Val Gly Leu Phe Tyr Phe Pro Asp Ala Phe Asn Ser<br>      340                        345                   350 | 1056 |

```
gct cca cga gaa gtt ggg ctt ttc tac ttc cct gat gct ttc aat agc     1056
Ala Pro Arg Glu Val Gly Leu Phe Tyr Phe Pro Asp Ala Phe Asn Ser
        340                     345                     350 cca tct aat tat gtt cgt cgt cag ata cca tct gag tat gaa cca gat     1104
Pro Ser Asn Tyr Val Arg Arg Gln Ile Pro Ser Glu Tyr Glu Pro Asp
                355                     360                     365 gcg gca gag cca tgc atc aag tac tat gac ggt gta tta tac ctt atc     1152
Ala Ala Glu Pro Cys Ile Lys Tyr Tyr Asp Gly Val Leu Tyr Leu Ile
370                     375                     380 act cgt ggt act cgt ggc gac cga cta gga agc tct ctg cat cgt agt     1200
Thr Arg Gly Thr Arg Gly Asp Arg Leu Gly Ser Ser Leu His Arg Ser
385                     390                     395                     400 aga gat ata ggt cag act tgg gag tca cta aga ttt cca cat aat gtg     1248
Arg Asp Ile Gly Gln Thr Trp Glu Ser Leu Arg Phe Pro His Asn Val
            405                     410                     415 cat cat act act tta ccg ttt gct aag gta gga gat gac ctt att atg     1296
His His Thr Thr Leu Pro Phe Ala Lys Val Gly Asp Asp Leu Ile Met
                420                     425                     430 ttt ggt tca gaa cgt gca gaa aat gaa tgg gaa gca ggt gca cca gat     1344
Phe Gly Ser Glu Arg Ala Glu Asn Glu Trp Glu Ala Gly Ala Pro Asp
                    435                     440                     445 gat cgt tac aag gca tct tat cct cgt acc ttc tat gca cga ttg aat     1392
Asp Arg Tyr Lys Ala Ser Tyr Pro Arg Thr Phe Tyr Ala Arg Leu Asn
450                     455                     460 gta aac aat tgg aat gca gat gat att gaa tgg gtt aac atc aca gac     1440
Val Asn Asn Trp Asn Ala Asp Asp Ile Glu Trp Val Asn Ile Thr Asp
465                     470                     475                     480 caa atc tat cag ggt gac att gtg aac tct agt gta ggt gta ggt tct     1488
Gln Ile Tyr Gln Gly Asp Ile Val Asn Ser Ser Val Gly Val Gly Ser
                485                     490                     495 gtt gta gtt aaa gac agc ttc att tac tat atc ttt ggt ggt gaa aac     1536
Val Val Val Lys Asp Ser Phe Ile Tyr Tyr Ile Phe Gly Gly Glu Asn
                500                     505                     510 cat ttc aac cca atg act tat ggt gac aac aaa gac aaa gac cca ttt     1584
His Phe Asn Pro Met Thr Tyr Gly Asp Asn Lys Asp Lys Asp Pro Phe
                    515                     520                     525 aaa ggt cat gga cac cct act gat ata tac tgc tat aag atg cag att     1632
Lys Gly His Gly His Pro Thr Asp Ile Tyr Cys Tyr Lys Met Gln Ile
530                     535                     540 gca aat gac aat cgt gta tct cgt aag ttt aca tat ggt gca act cca     1680
Ala Asn Asp Asn Arg Val Ser Arg Lys Phe Thr Tyr Gly Ala Thr Pro
545                     550                     555                     560 ggt caa gct ata cct act ttc atg ggt act gat gga ata cga aat atc     1728
Gly Gln Ala Ile Pro Thr Phe Met Gly Thr Asp Gly Ile Arg Asn Ile
                565                     570                     575 cct gca cct ttg tat ttc tca gat aac att gtt aca gag gat act aaa     1776
Pro Ala Pro Leu Tyr Phe Ser Asp Asn Ile Val Thr Glu Asp Thr Lys
                    580                     585                     590 gtt gga cac tta aca ctt aaa gca agc aca agt gcc aat ata cga tct     1824
Val Gly His Leu Thr Leu Lys Ala Ser Thr Ser Ala Asn Ile Arg Ser
                595                     600                     605 gaa atg cag atg gaa ggt gag tat ggc ttt att ggc aag tct gtt cca     1872
Glu Met Gln Met Glu Gly Glu Tyr Gly Phe Ile Gly Lys Ser Val Pro
610                     615                     620 aag gac aaa cca aca ggt caa cgt ttg att att tgt ggt gga gaa ggg     1920
Lys Asp Lys Pro Thr Gly Gln Arg Leu Ile Ile Cys Gly Gly Glu Gly
625                     630                     635                     640 act tca tca tct tca ggt gca cag ata act ttg cac ggt tct aat tca     1968
Thr Ser Ser Ser Ser Gly Ala Gln Ile Thr Leu His Gly Ser Asn Ser
                645                     650                     655
```

```
agt aat gct aag cgt atc act tat aac gga aac gag cac cta ttc caa   2016
Ser Asn Ala Lys Arg Ile Thr Tyr Asn Gly Asn Glu His Leu Phe Gln
            660                 665                 670 ggt gca cca atc atg cct gct gta gat aac cag ttt gct gct ggt gga   2064
Gly Ala Pro Ile Met Pro Ala Val Asp Asn Gln Phe Ala Ala Gly Gly
                675                 680                 685 cct agt aac cga ttc act acc atc tac cta ggc agt gac cct gtt aca   2112
Pro Ser Asn Arg Phe Thr Thr Ile Tyr Leu Gly Ser Asp Pro Val Thr
        690                 695                 700 act tca gat gct gac cac aag tac ggt atc tct agt att aat acc aag   2160
Thr Ser Asp Ala Asp His Lys Tyr Gly Ile Ser Ser Ile Asn Thr Lys
705                 710                 715                 720 gtg tta aag gct tgg agc agg gtt ggt ttt aaa cag tat ggt ttg aat   2208
Val Leu Lys Ala Trp Ser Arg Val Gly Phe Lys Gln Tyr Gly Leu Asn
                725                 730                 735 agt gaa gca gag agg aac ctt gat agc ata cac ttc ggt gtc ttg gct   2256
Ser Glu Ala Glu Arg Asn Leu Asp Ser Ile His Phe Gly Val Leu Ala
            740                 745                 750 cag gat att gta gct gct ttt gaa gct gaa ggg ttg gat gcc att aag   2304
Gln Asp Ile Val Ala Ala Phe Glu Ala Glu Gly Leu Asp Ala Ile Lys
        755                 760                 765 tat gga att gtg tcc ttc gaa gaa ggt agg tat ggt gtg aga tat agt   2352
Tyr Gly Ile Val Ser Phe Glu Glu Gly Arg Tyr Gly Val Arg Tyr Ser
770                 775                 780 gaa gtt cta atc cta gag gct gcc tat act cgc cat cgt ctt gat aaa   2400
Glu Val Leu Ile Leu Glu Ala Ala Tyr Thr Arg His Arg Leu Asp Lys
                785                 790                 795                 800 tta gag gag atg tat gcc act aat aaa atc agt taa                   2436
Leu Glu Glu Met Tyr Ala Thr Asn Lys Ile Ser
            805                 810

<210> SEQ ID NO 2
<211> LENGTH: 811
<212> TYPE: PRT
<213> ORGANISM: Bacteriophage E

<400> SEQUENCE: 2

Met Ile Gln Arg Leu Gly Ser Ser Leu Val Lys Phe Lys Ser Lys Ile
1               5                   10                  15

Ala Gly Ala Ile Trp Arg Asn Leu Asp Asp Lys Leu Thr Glu Val Val
            20                  25                  30

Ser Leu Lys Asp Phe Gly Ala Lys Gly Asp Gly Lys Thr Asn Asp Gln
        35                  40                  45

Asp Ala Val Asn Ala Ala Met Ala Ser Gly Lys Arg Ile Asp Gly Ala
    50                  55                  60

Gly Ala Thr Tyr Lys Val Ser Ser Leu Pro Asp Met Glu Arg Phe Tyr
65                  70                  75                  80

Asn Thr Arg Phe Val Trp Glu Arg Leu Ala Gly Gln Pro Leu Tyr Tyr
                85                  90                  95

Val Ser Lys Gly Phe Ile Asn Gly Glu Leu Tyr Lys Ile Thr Asp Asn
            100                 105                 110

Pro Tyr Tyr Asn Ala Trp Pro Gln Asp Lys Ala Phe Val Tyr Glu Asn
        115                 120                 125

Val Ile Tyr Ala Pro Tyr Met Gly Ser Asp Arg His Gly Val Ser Arg
    130                 135                 140

Leu His Val Ser Trp Val Lys Ser Gly Asp Asp Gly Gln Thr Trp Ser
145                 150                 155                 160
```

-continued

```
Thr Pro Glu Trp Leu Thr Asp Met His Pro Asp Tyr Pro Thr Val Asn
            165                 170                 175

Tyr His Cys Met Ser Met Gly Val Cys Arg Asn Arg Leu Phe Ala Met
            180                 185                 190

Ile Glu Thr Arg Thr Leu Ala Lys Asn Glu Leu Thr Asn Cys Ala Leu
            195                 200                 205

Trp Asp Arg Pro Met Ser Arg Ser Leu His Leu Thr Gly Gly Ile Thr
            210                 215                 220

Lys Ala Ala Asn Gln Arg Tyr Ala Thr Ile His Val Pro Asp His Gly
225                 230                 235                 240

Leu Phe Val Gly Asp Phe Val Asn Phe Ser Asn Ser Ala Val Thr Gly
            245                 250                 255

Val Ser Gly Asp Met Lys Val Ala Thr Val Ile Asp Lys Asp Asn Phe
            260                 265                 270

Thr Val Leu Thr Pro Asn Gln Gln Thr Ser Asp Leu Asn Asn Ala Gly
            275                 280                 285

Lys Asn Trp His Met Gly Thr Ser Phe His Lys Ser Pro Trp Arg Lys
            290                 295                 300

Thr Asp Leu Gly Leu Ile Pro Arg Val Thr Glu Val His Ser Phe Ala
305                 310                 315                 320

Thr Ile Asp Asn Asn Gly Phe Val Met Gly Tyr His Gln Gly Asp Val
            325                 330                 335

Ala Pro Arg Glu Val Gly Leu Phe Tyr Phe Pro Asp Ala Phe Asn Ser
            340                 345                 350

Pro Ser Asn Tyr Val Arg Arg Gln Ile Pro Ser Glu Tyr Glu Pro Asp
            355                 360                 365

Ala Ala Glu Pro Cys Ile Lys Tyr Tyr Asp Gly Val Leu Tyr Leu Ile
            370                 375                 380

Thr Arg Gly Thr Arg Gly Asp Arg Leu Gly Ser Ser Leu His Arg Ser
385                 390                 395                 400

Arg Asp Ile Gly Gln Thr Trp Glu Ser Leu Arg Phe Pro His Asn Val
            405                 410                 415

His His Thr Thr Leu Pro Phe Ala Lys Val Gly Asp Asp Leu Ile Met
            420                 425                 430

Phe Gly Ser Glu Arg Ala Glu Asn Glu Trp Glu Ala Gly Ala Pro Asp
            435                 440                 445

Asp Arg Tyr Lys Ala Ser Tyr Pro Arg Thr Phe Tyr Ala Arg Leu Asn
450                 455                 460

Val Asn Asn Trp Asn Ala Asp Asp Ile Glu Trp Val Asn Ile Thr Asp
465                 470                 475                 480

Gln Ile Tyr Gln Gly Asp Ile Val Asn Ser Val Gly Val Gly Ser
            485                 490                 495

Val Val Val Lys Asp Ser Phe Ile Tyr Tyr Ile Phe Gly Gly Glu Asn
            500                 505                 510

His Phe Asn Pro Met Thr Tyr Gly Asp Asn Lys Asp Lys Asp Pro Phe
            515                 520                 525

Lys Gly His Gly His Pro Thr Asp Ile Tyr Cys Tyr Lys Met Gln Ile
            530                 535                 540

Ala Asn Asp Asn Arg Val Ser Arg Lys Phe Thr Tyr Gly Ala Thr Pro
545                 550                 555                 560

Gly Gln Ala Ile Pro Thr Phe Met Gly Thr Asp Gly Ile Arg Asn Ile
            565                 570                 575

Pro Ala Pro Leu Tyr Phe Ser Asp Asn Ile Val Thr Glu Asp Thr Lys
```

```
            580                 585                 590
Val Gly His Leu Thr Leu Lys Ala Ser Thr Ser Ala Asn Ile Arg Ser
            595                 600                 605

Glu Met Gln Met Glu Gly Glu Tyr Gly Phe Ile Gly Lys Ser Val Pro
        610                 615                 620

Lys Asp Lys Pro Thr Gly Gln Arg Leu Ile Ile Cys Gly Gly Glu Gly
625                 630                 635                 640

Thr Ser Ser Ser Gly Ala Gln Ile Thr Leu His Gly Ser Asn Ser
                645                 650                 655

Ser Asn Ala Lys Arg Ile Thr Tyr Asn Gly Asn Glu His Leu Phe Gln
                660                 665                 670

Gly Ala Pro Ile Met Pro Ala Val Asp Asn Gln Phe Ala Ala Gly Gly
            675                 680                 685

Pro Ser Asn Arg Phe Thr Thr Ile Tyr Leu Gly Ser Asp Pro Val Thr
        690                 695                 700

Thr Ser Asp Ala Asp His Lys Tyr Gly Ile Ser Ser Ile Asn Thr Lys
705                 710                 715                 720

Val Leu Lys Ala Trp Ser Arg Val Gly Phe Lys Gln Tyr Gly Leu Asn
                725                 730                 735

Ser Glu Ala Glu Arg Asn Leu Asp Ser Ile His Phe Gly Val Leu Ala
                740                 745                 750

Gln Asp Ile Val Ala Ala Phe Glu Ala Glu Gly Leu Asp Ala Ile Lys
            755                 760                 765

Tyr Gly Ile Val Ser Phe Glu Glu Gly Arg Tyr Gly Val Arg Tyr Ser
        770                 775                 780

Glu Val Leu Ile Leu Glu Ala Ala Tyr Thr Arg His Arg Leu Asp Lys
785                 790                 795                 800

Leu Glu Glu Met Tyr Ala Thr Asn Lys Ile Ser
                805                 810

<210> SEQ ID NO 3
<211> LENGTH: 45
<212> TYPE: DNA
<213> ORGANISM: Artificial Sequence
<220> FEATURE:
<221> NAME/KEY: CDS
<222> LOCATION: (1)..(39)
<220> FEATURE:
<223> OTHER INFORMATION: Description of Artificial Sequence:pGEX-2T has
      the sequence

<400> SEQUENCE: 3 ctg gtt ccg cgt gga tcc ccg gga att cat cgt gac tga ctgacg          45
Leu Val Pro Arg Gly Ser Pro Gly Ile His Arg Asp
 1               5                  10

<210> SEQ ID NO 4
<211> LENGTH: 12
<212> TYPE: PRT
<213> ORGANISM: Artificial Sequence

<400> SEQUENCE: 4

Leu Val Pro Arg Gly Ser Pro Gly Ile His Arg Asp
 1               5                  10

<210> SEQ ID NO 5
<211> LENGTH: 23
<212> TYPE: DNA
<213> ORGANISM: Artificial Sequence
<220> FEATURE:
```

-continued

```
<223> OTHER INFORMATION: Description of Artificial Sequence:Degenerate
      oligonucleotide probe

<400> SEQUENCE: 5
taycaycagg gkgaygtkgc scc                                              23

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:
      Non-degenerate oligonucleotide

<400> SEQUENCE: 6
gatcttggtc taatccct                                                    18

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 7
ccggggatcc atgattcaaa gactaggttc ttcatta                               37

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence:Primer

<400> SEQUENCE: 8
cacagaattc tatgtgttct ggcgtgcagc agattgc                               37
```